United States Patent
Florin et al.

(10) Patent No.: US 8,921,087 B2
(45) Date of Patent: Dec. 30, 2014

(54) COCOA SOMATIC EMBRYOGENESIS

(75) Inventors: Bruno Jean-Marie Florin, St. Cyr-sur-Loire (FR); Bernard Masseret, Notre Dame d'Oe (FR); Caroline Denise Monique Vachet, La Riche (FR)

(73) Assignee: Nestec S.A., Vevey (CH)

(*) Notice: Subject to any disclaimer, the term of this patent is extended or adjusted under 35 U.S.C. 154(b) by 283 days.

(21) Appl. No.: 12/745,753

(22) PCT Filed: Dec. 1, 2008

(86) PCT No.: PCT/EP2008/010171
§ 371 (c)(1),
(2), (4) Date: Jun. 2, 2010

(87) PCT Pub. No.: WO2009/071254
PCT Pub. Date: Jun. 11, 2009

(65) Prior Publication Data
US 2010/0236143 A1  Sep. 23, 2010

(30) Foreign Application Priority Data
Dec. 4, 2007 (EP) ..................................... 07122289

(51) Int. Cl.
*A01H 4/00* (2006.01)

(52) U.S. Cl.
CPC ..................................... *A01H 4/005* (2013.01)
USPC .................................. 435/240.49; 435/240.45

(58) Field of Classification Search
CPC ....... A01H 4/001; A01H 4/008; A01H 4/005; A23G 1/00
See application file for complete search history.

(56) References Cited

U.S. PATENT DOCUMENTS 5,312,801 A * 5/1994 Sondahl et al. ............ 435/430.1
6,444,467 B1 * 9/2002 Fan et al. .................... 435/430.1

FOREIGN PATENT DOCUMENTS

WO  WO9312645  7/1993
WO  WO9900487  1/1999

OTHER PUBLICATIONS

Young et al. Cacao tissue culture protocol book. Version 1.4 Jan. 27, 2003 p. 1-31.*
Zhijian et al. Somatic embryogenesis and plant regenerationfrom floral explants of cacao using thidiazuron. In Vitro Cell. Dev. Bio Plant 34: 293-299 1998.*
Traore et al. Micropropagation of *Theobroma cacao* L using somatic embryo-derived plants. In Vitro Cell, Dev. Bio. Plant 39:332-337, 2003.*
Niemenak et al. Regeneration of Somatic embryos in *Theobroma cacao* L. In temporary immersion bioreactor and analyses of free amino acids in different tissues. Plant Cell Reports Springer-Verlag 2008.*
Young et al. Cacao Tissue Protocol Book 2003.*
Traore et al. In Vitro Cell Dev. Bio. Plant 39 : 332-337 2003.*
Ducos et al. Bioreactors for Coffe Mass Propagation by Somatic Embryogenesis. International Journal of Plant Developmental Biology 2007.*
Lopez-Baez, et al., "Embryogenese Somatique De Cacaoyer *Theobroma cacao* L. A Partir De Pieces Florales, Somatic Embryogenesis and Plant Regeneration from Flower Parts of Cocoa *Theobroma cacao* L," Comptes Rendls Des Seances De L'Academie Des Sciences, Serie III: Sciences de la Vie, vol. 316, Jan. 1993, pp. 579-584, XP002913516.
Zhijian et al., "Somatic embryogenesis and plant regeneration from floral explants of *cacao (Theobroma cacao* L.) using thidiazuron," In Vitro Cellular and Developmental Biology Plant, vol. 34, No. 4, Oct. 1998, pp. 293-299, XP009099567.
Alemanno et al., "A comparison between *Theobroma cacao* L. zygotic embryogenesis and somatic embryogenesis from flora explants," In Vitro Cellular and Developmental Biology Plant, vol. 33, No. 3, 1997, pp. 163-172, XP009099568.
Maximova et al., "Efficiency, genotypic variability, and cellular origin of primary and secondary somatic embryogenesis of *Theobroma cacao* L." In Vitro Cellular and Developmental Biology Plant, vol. 38, No. 3, May 2002, pp. 252-259, XP009099566.

* cited by examiner

*Primary Examiner* — Annette Para
(74) *Attorney, Agent, or Firm* — K&L Gates LLP

(57) ABSTRACT

A process for the propagation of *Theobroma cacao* L. by somatic embryogenesis using explant material which is subjected to a) primary embryogenesis in the dark in a solid culture medium causing induction and expression to produce primary embryos, b) secondary embryogenesis i) in which the primary embryos are treated in the dark in a solid or liquid culture medium to produce and multiply embryogenic callus followed by ii) treatment of the embryogenic callus in the dark in a suitable liquid culture medium causing expression of the embryogenic callus to produce further new secondary embryos, c) pre-germination of the secondary embryos in a Petri dish on a solid medium, or in a bioreactor in a liquid medium, into pre-germinated secondary embryos at the cotyledonary stage, d) ex-vitro germination of the pre-germinated secondary embryos at the cotyledonary stage by sowing directly on a culture substrate in the greenhouse to produce the plantlets, and e) development of the plantlets.

11 Claims, No Drawings

COCOA SOMATIC EMBRYOGENESIS

FIELD OF THE INVENTION

The present invention relates to in vitro multiplication and plant regeneration of *Theobroma cacao* L. to achieve clonal propagation at large scale (or pre-commercial) level by somatic embryogenesis.

BACKGROUND OF THE INVENTION

*Theobroma cacao* L. is a tropical tree of important economic interest for many countries. Cocoa is mainly allogamous and propagated from cross-pollinated seeds leading to plantations which are often established with unselected seedlings resulting in great heterogeneity, whereby only 10% to 20% of the trees produce 60% to 80% of the cocoa beans. Therefore vegetative propagation of selected plants would be desirable, but conventional methods such as cutting or grafting often present growth defaults. In such clonal plantations, cocoa plants are shorter and tend to present an increased growth of side shoots, as well as some branches being very close above the soil. Pruning is needed in order to correct and lift the crown of such trees. Moreover, these propagation methods are difficult to apply on a large-scale commercial basis.

Somatic embryogenesis is a type of vegetative propagation based on plant cell totipotency which offers a powerful alternative to other vegetative propagation methods, e.g. cutting or grafting.

Regardless of the plant species, somatic embryogenesis generally involves a) induction of embryogenic calli followed by their identification and selection by physical isolation,
b) multiplication of embryogenic cells,
c) regeneration of large numbers of embryos from these cells (embryogenic phase), and
d) conversion of these embryos into mature embryos able to regenerate a plant.

Propagation of *Theobroma cacao* L. by somatic embryogenesis in solid gel media is known using cocoa flower buds which are subjected to a) primary embryogenesis in a Petri dish for 9 weeks in the dark at 25° C. in a suitable solid gel culture medium causing induction and expression to produce primary embryos,
b) secondary embryogenesis in a Petri dish
   i) for 9-16 weeks in the dark at 25° C. in a suitable solid gel culture medium to produce embryogenic callus followed by
   ii) 2×3 weeks (whereby the calli are transplanted and sub-cultivated in a fresh medium after 3 weeks) in the dark at 25° C. in a suitable solid gel culture medium causing expression to produce further new secondary embryos,
c) maturation of the secondary embryos into plantlets for 4-6 weeks in the light at 30° C./25° C. in a solid gel maturation medium,
d) in vitro development for 4-8 weeks in the light at 25° C. in a solid gel culture medium.

The developed plantlets are then transplanted in the greenhouse for plant acclimatization, then the nursery before going to field where they grow into cocoa trees.

The compositions of the basal culture media are well known to persons skilled in the art and they are made solid by the use of a gel such as agar or gelrite. The culture medium may be any one of those described in Driver & Kuniyuki, Hortscience 19 (1984), 507-509; Yasuda, Fuji and Yamaguchi, Plant Cell Physiol. 26 (1985), 595-597; Murashige T. and Skoog., Physiol. Plant. 15 (1962), 473-497, Berthouly M. and Michaux-Ferriere N., Plant Cell Tiss. Org. Cult. 44 (1996), 169-176 and Halperin, W. 146 (1964), 408-410, Lloyd & Mc Cown, WPM, Basal salts Int. Plant Prop. Soc. Proc. Vol. 30 (421-427) 1981 Vitamins Mullin & al. Phytopath. Vol. 64 (1425-1429) 1974, which documents are incorporated herein by way of reference. The composition of the basal media and some growth hormones for the propagation of *Theobroma cacao* L. by somatic embryogenesis is not the same as for coffee plants but suitable media compositions would be readily ascertainable by persons skilled in the art.

Successful multiplication of the embryonic calli by somatic embryogenesis using a solid gel nutrient medium has permitted a significant production of "in vitro" cocoa trees which are more vigorous (trunk diameter), produce earlier fruiting, are earlier in bearing pods, are more drought tolerant, give an improved yield of the first crops of the trees produced, and only require half the pruning work, compared with cocoa trees derived by grafting or cutting. However, it is still desirable to improve the propagation even further in order to grow cocoa trees on a commercial scale.

Although vegetative propagation of coffee plants by somatic embryogenesis using both solid nutrient culture media and liquid nutrient culture media is known, the use of liquid nutrient culture media for the vegetative propagation of cocoa plants by somatic embryogenesis is not known. Cocoa embryos are larger than coffee embryos and much more fragile and it is important to limit the handling of the embryos which is carried out using forceps and leads to high labour costs. This is different from coffee because coffee embryos produce smaller cotyledons and thus can be transferred from one medium to another one without damaging them.

SUMMARY OF THE PRESENT INVENTION

We have surprisingly found that the use of liquid nutrient culture media for the vegetative propagation of cocoa plants by somatic embryogenesis improves the multiplication of embryonic calli, as well as providing a significant increase in the production of in vitro cocoa plants compared with the use of solid media.

According to the present invention there is provided a process for the propagation of *Theobroma cacao* L. by somatic embryogenesis using explant material which is subjected to a) primary embryogenesis in the dark in a solid culture medium causing induction and expression to produce primary embryos,
b) secondary embryogenesis
   i) in which the primary embryos are treated in the dark in a solid or liquid culture medium to produce and multiply embryogenic callus followed by
   ii) treatment of the embryogenic callus in the dark in a suitable liquid culture medium causing expression of the embryogenic callus to produce further new secondary embryos,
c) pre-germination of the secondary embryos in a Petri dish on a solid medium, or in a bioreactor in a liquid medium, into pre-germinated secondary embryos at the cotyledonary stage,
d) ex-vitro germination of the pre-germinated secondary embryos at the cotyledonary stage by sowing directly on a culture substrate in the greenhouse to produce the plantlets, and e) development of the plantlets.

DETAILED DESCRIPTION OF THE INVENTION

The explant material may conveniently be obtained, for example, from the flower buds by using staminodes & petals & leaves.

The culture media used generally comprise macro- and micro-nutrients together with vitamins, growth hormones, glucose and/or sucrose. If the medium is solid it also contains a gelling agent such as agar or gelrite.

The primary embryogenesis of step (a) to produce primary embryos is conveniently carried out in a petri dish over a suitable time period which may be from 5 to 15 weeks and preferably from 7 to 12 weeks. The temperature may be from 20° C. to 30° C. and preferably from 24° C. to 27° C.

Step (a) may be carried out in more than one stage, e.g. in a Petri dish for the first stage in a first culture medium to produce primary callus, transfer to a second Petri dish for the second stage in a second culture medium to produce embryonic callus, and transfer to a third Petri dish for the third stage in a third culture medium to produce primary embryos. In the third stage, the culture medium may advantageously be replenished about half way through the treatment.

The first and second culture media contain phytohormones (or growth regulators), for example 2,4-D, TDZ, kinetin, which are key for the induction of somatic embryogenesis in the first and second stage, and in the third medium growth hormones are absent to facilitate embryo differentiation in the third stage.

For example, when the explant material is obtained from flower buds, 1 to 10 and preferably 2 to 5 flower buds may be used in a Petri dish, e.g. of 5 cm diameter in 10 ml medium.

The secondary embryogenesis of step b (i) to produce and multiply the embryogenic callus is conveniently carried out in a Petri dish or Erlenmeyer flask over a suitable time period which may be from 10 to 25 weeks and preferably from 8 to 22 weeks. The temperature may be from 20° C. to 30° C. and preferably from 24° C. to 27° C. A degree of multiplication of 1.5 to 3 may be achieved for the embryonic callus.

If desired or necessary, the embryonic callus may be stored by freezing in liquid nitrogen for future use.

The treatment of the embryogenic callus in step b (ii) to cause expression to produce further new secondary embryos is conveniently carried out in an Erlenmeyer flask or a bioreactor having a capacity of from 250 ml to 10 liters preferably in a 250 ml Erlenmeyer flask over a period of 1-6 weeks, preferably 3 weeks. The temperature may be from 20° C. to 30° C. and preferably from 24° C. to 27° C. The treatment in an Erlenmeyer flask is preferably carried out with agitation, e.g. stirring on a rotary shaker at 120 revolutions per minute.

The treatment of the secondary embryos in step (c) to cause pre-germination to produce further pre-germinated embryos at cotyledonary stage is carried out in a Petri dish in a solid nutrient medium or in a liquid nutrient medium either in an Erlenmeyer flask or in a temporary immersion bioreactor over a period of 3-12 weeks, preferably 6-9 weeks in temporary immersion bioreactor whereby about half way through the treatment, the nutrient medium is replenished. The temperature may be from 20° C. to 30° C. and preferably 25° C. Preferably, the treatment of the embryogenic callus of step (b, ii+c) is carried out over a total period of 9-12 weeks whereby about half way through the treatment, the nutrient medium is replenished.

Thus, an advantage of the present invention by using a liquid medium in step b (ii) and (c) that the germination may take place ex-vitro, i.e. the pre-germinated secondary embryos at cotyledonary stage may be sown directly on a culture substrate in the greenhouse whereupon they germinate to produce the plantlets. This eliminates the separate in-vitro germination stage in the known process. The culture substrate may be, for example, a mixture comprising vermiculite/perlite, coco peat, etc.

The plantlets are then transplanted in the nursery, finally in the field and grown into cocoa trees Further advantages of the use of a liquid medium instead of a solid medium for the multiplication of the embryogenic callus and for the expression and the pre-germination of embryos are as follows:

i) improves the multiplication of embryonic calli, ii) improves the synchronisation of the occurrence and development of the embryos iii) by allowing the direct "ex-vitro" conversion of the secondary embryos into plantlets, the individual manipulation of the embryos under "in-vitro" conditions is avoided which enables a drastic reduction of work under sterile conditions, iv) provides a significant increase in the production of in vitro cocoa plants, and v) the liquid medium is cheaper owing to the elimination of agar or gelrite for solidification, leading to lower costs (especially labour costs), and better synchronicity of the embryo development because there is a better homogeneity of the development stage among the embryo population).

EXAMPLE

The following Example further illustrates the present invention.

Example 1

5 flower buds are cultured in a Petri dish of 5 cm diameter in 10 ml medium comprising macro-nutrients (DKW/Hortscience 19. 1984), micro-nutrients DKW, vitamins DKW, Glucose 20 g/l, Glutamine 250 mg/l, Myo-Inositol 100 mg/l, 2,4-D 2 mg/l, TDZ 5 µg/l, Gelrite 3 g/l for 2 weeks at 25° C. in the dark to produce primary callus.

The primary callus are transferred to a second Petri dish of 5 cm diameter in 10 ml medium comprising macro-nutrients WPM, micro-nutrients WPM, vitamins B5, glucose 20 g/l, 2,4-D 2 mg/l, Kinetin 0.25 mg/l for 2 weeks at 25° C. in the dark to produce embryogenic callus.

The embryogenic callus are transferred to a third Petri dish of 5 cm diameter in 10 ml medium comprising macro-nutrients DKW, micro-nutrients DKW, vitamins DKW, glucose 1 g/l, sucrose 30 g/l for 2×3 weeks at 25° C. in the dark to produce about 5 to 30 primary embryos.

The primary embryos are transferred to a fourth Petri dish of 5 cm diameter in 10 ml medium comprising macro-nutrients (Murashige and Skoog. 1962), micro-nutrients DKW, vitamins DKW, 2,4,5-T 1 mg/l, adenine 0.25 mg/l, Glucose 30 g/l, L-lysine 400 mg/l, L-leucin 400 mg/l, L-arginin 400 mg/l, L-tryptophan 200 mg/l, Gelrite 3 g/l for 15 weeks at 25° C. in the dark to produce secondary embryogenic callus with a degree of multiplication of 1.5 to 3.

The embryonic callus is transferred to a 250 ml Erlenmeyer flask containing a liquid medium comprising macro-nutrients (Murashige and Skoog. 1962), micro-nutrients DKW, vitamins DKW, glucose 30 g/l, adenine 0.025 mg/l, L-lysine 400 mg/l, L-leucin 400 mg/l, L-arginin 400 mg/l, L-tryptophan 200 mg/l and cultured over a period of 3 weeks causing expression of the embryogenic callus to produce further new secondary embryos.

The secondary embryos are then pre-germinated in a temporary immersion 5 liter bioreactor containing liquid medium comprising macro-nutrients/2 (Murashige and Skoog. 1962), micro-nutrients DKW/2, vitamins DKW, glucose 10 g/l, sucrose 5 g/l and cultured over 6 to 9 weeks at 25° C. whereby about half way through the treatment, the nutrient medium is replenished.

In step (d) the pre-germinated secondary embryos at cotyledonary stage are then sown on a substrate comprising Blond sphagnum peat+perlite 15%+vermiculite 10% in the greenhouse.

The whole process takes from about 30-40 weeks to about one year from in vitro induction to greenhouse.

The invention claimed is:

1. A process for the propagation of *Theobroma cacao* L. by somatic embryogenesis, the process comprising:
   a) primary embryogenesis for 5 to 15 weeks at a temperature from 20° C. to 30° C.
   i) in which explant material is treated in the dark on a solid culture medium containing a phyotohormone selected from the group consisting of 2,4-Dichlorophenoxyacetic acid (2,4-D), Thidiazuron (TDZ), kinetin, and combinations thereof to produce primary callus followed by
   ii) treatment of the primary callus in the dark on a solid culture medium containing a phyotohormone selected from the group consisting of 2,4-Dichlorophenoxyacetic acid (2,4-D), Thidiazuron (TDZ), kinetin, and combinations thereof to produce primary embryonic callus followed by
   iii) treatment of the primary embryonic callus in the dark on a solid culture medium that is free of growth hormones to produce primary embryos,
   b) secondary embryogenesis
   i) in which the primary embryos are treated in the dark in a culture medium selected from the group consisting of solid and liquid culture medium for 10 to 25 weeks at a temperature from 20° C. to 30° C. to produce and multiply secondary embryogenic callus followed by
   ii) treatment of the secondary embryogenic callus in the dark in a suitable liquid culture medium for 1 to 6 weeks at a temperature from 20° C. to 30° C. to produce secondary embryos,
   c) pre-germination of the secondary embryos in a liquid medium in a bioreactor for 3 to 12 weeks at a temperature from 20° C. to 30° C. to produce pre-germinated secondary embryos at the cotyledonary stage,
   d) ex-vitro germination of the pre-germinated secondary embryos at the cotyledonary stage by sowing directly on a culture substrate in a greenhouse to produce plantlets, and
   e) development of the plantlets;
   wherein the embryogenic calli are obtained from flower buds.

2. The process of claim 1, wherein the primary embryogenesis of step (a) is performed over a time period of from 7 to 12 weeks.

3. The process of claim 1, wherein the primary embryogenesis of step (a) is performed at a temperature of from 24° C. to 27° C.

4. The process of claim 1, wherein the secondary embryogenesis of step (b, i) is performed over a time period of from 10 to 22 weeks.

5. The process of claim 1, wherein the secondary embryogenesis of step (b, i) is performed at a temperature of from 24° C. to 27° C.

6. The process of claim 1, wherein the treatment of the embryogenic callus of step (b, ii+c) is performed over a period of 9-12 weeks whereby about half way through the treatment, a nutrient medium is replenished.

7. The process of claim 1, wherein the plantlets are then transplanted in a nursery, finally in a field and grown into cocoa trees.

8. The process of claim 1, wherein step (b, i) of secondary embryogenesis is carried out from 10 to 22 weeks at 24° C. to 27° C.

9. The process of claim 1, wherein step (b, ii) of secondary embryogenesis is carried out for 3 weeks at 24° C. to 27° C.

10. The process of claim 1, wherein the pre-germination in step (c) is performed from 6 to 9 weeks at 25° C.

11. A process for the propagation of *Theobroma cacao* L. by somatic embryogenesis, the process comprising:
   a) primary embryogenesis for 5 to 15 weeks at a temperature from 20° C. to 30° C.
   i) in which explant material is treated in the dark on a solid culture medium to produce primary callus followed by
   ii) treatment of the primary callus in the dark on a solid culture medium to produce primary embryonic callus followed by
   iii) treatment of the primary embryonic callus in the dark on a solid culture medium to produce primary embryos,
   the culture medium in the production of the primary callus in step (a, i) and the culture medium in the production of the primary embryonic callus in step (a, ii) both containing phytohormones, and growth hormones absent in the culture medium in the production of the primary embryos in step (a, iii);
   b) secondary embryogenesis
   i) in which the primary embryos are treated in the dark in a culture medium selected from the group consisting of solid and liquid culture medium for 10 to 25 weeks at a temperature from 20° C. to 30° C. to produce and multiply secondary embryogenic callus followed by
   ii) treatment of the secondary embryogenic callus in the dark in a suitable liquid culture medium for 1 to 6 weeks at a temperature from 20° C. to 30° C. to produce secondary embryos,
   the embryogenic calli obtained from flower buds;
   c) pre-germination of the secondary embryos in a liquid medium in a bioreactor for 3 to 12 weeks at a temperature from 20° C. to 30° C. to produce pre-germinated secondary embryos at the cotyledonary stage;
   d) ex-vitro germination of the pre-germinated secondary embryos at the cotyledonary stage by sowing directly on a culture substrate in a greenhouse to produce plantlets; and
   e) development of the plantlets.

* * * * *